US012465385B1

(12) United States Patent
Chen

(10) Patent No.: US 12,465,385 B1
(45) Date of Patent: Nov. 11, 2025

(54) FOOT REPAIR DEVICE

(71) Applicant: Dixing Chen, Shenzhen (CN)

(72) Inventor: Dixing Chen, Shenzhen (CN)

( * ) Notice: Subject to any disclaimer, the term of this patent is extended or adjusted under 35 U.S.C. 154(b) by 0 days.

(21) Appl. No.: 19/204,002

(22) Filed: May 9, 2025

(30) Foreign Application Priority Data

Apr. 29, 2025 (CN) ......................... 202520833286.5

(51) Int. Cl.
*A61B 17/00* (2006.01)
*A61B 17/32* (2006.01)

(52) U.S. Cl.
CPC .... *A61B 17/32* (2013.01); *A61B 2017/00389* (2013.01); *A61B 2017/00398* (2013.01); *A61B 2017/00734* (2013.01); *A61B 2017/320004* (2013.01)

(58) Field of Classification Search
CPC .......... A61B 17/32; A61B 2017/00389; A61B 2017/00398; A61B 2017/00734; A61B 2017/320004
USPC ........ 173/197, 81, 90, 140, 141, 162.1, 198, 173/213, 168, 171
See application file for complete search history.

(56) References Cited

U.S. PATENT DOCUMENTS 1,984,256 A * 12/1934 Dederer ............... B25D 11/102 173/101
2,016,829 A * 10/1935 Dederer ............... B25D 16/006 173/205
3,802,698 A * 4/1974 Burian ................... A61B 5/222 482/8
3,835,715 A * 9/1974 Howell ................ B25D 11/106 173/48
4,105,084 A * 8/1978 Baak ..................... B62B 5/0026 180/21
4,220,996 A * 9/1980 Searcy ............... A63B 71/0686 377/5
4,889,108 A * 12/1989 Bond ..................... A63B 24/00 482/901
5,145,475 A * 9/1992 Cares ................... A63B 21/157 482/52
5,352,166 A * 10/1994 Chang ................ A63B 69/0048 482/52
5,538,486 A * 7/1996 France ............... A63B 21/4035 482/121
5,561,734 A * 10/1996 Simonsen .............. H01C 10/00 388/838

(Continued)

*Primary Examiner* — Robert F Long
(74) *Attorney, Agent, or Firm* — Birchwood IP

(57) ABSTRACT

A foot repair device is provided, which includes a housing, a foot repair device main body, and a functional head. The housing forms a handle, and the handle includes a first handle end and a second handle end. The foot repair device main body is accommodated in the housing and includes a driving motor, a power supply component, and a control component. The functional head is detachably connected to the driving motor, and the control component includes a control circuit board, a switch button, and a speed control dial. The speed control dial adjusts a rotation speed of the functional head by adjusting an output rotation speed of the driving motor. The present disclosure provides a reasonable layout of switch button and speed control dial, allowing a user to easily control the switch and adjust the speed without significantly moving their fingers during operation.

8 Claims, 7 Drawing Sheets

(56) References Cited

U.S. PATENT DOCUMENTS 6,508,313 B1 * 1/2003 Carney ............... B25B 23/1475 173/171
6,868,919 B1 * 3/2005 Manschitz ........... B25D 16/006 335/205
6,939,262 B1 * 9/2005 Yu ....................... F16H 37/0833 74/354
7,817,384 B2 * 10/2010 Woods .................. B24B 23/028 318/434
8,171,828 B2 * 5/2012 Duvan ................ B25B 23/1425 73/862.27
8,674,640 B2 * 3/2014 Suda ....................... B25B 21/02 173/4
8,678,106 B2 * 3/2014 Matsunaga ........... B25B 21/008 173/183
9,039,557 B2 * 5/2015 Naughton ........... B05C 17/0103 221/229
9,060,595 B2 * 6/2015 Grez ...................... A46B 13/00
9,993,259 B2 * 6/2018 Barnes ........... A61B 17/320036
10,206,731 B2 * 2/2019 Kust ..................... B25B 21/002
10,646,982 B2 * 5/2020 Dey, IV .................... B25F 5/00
12,122,029 B2 * 10/2024 Kamiya .................. B25B 23/18
2002/0050364 A1 * 5/2002 Suzuki ................ B25B 23/1405 173/1
2003/0079562 A1 * 5/2003 Schaible .............. B25D 16/006 74/473.37
2003/0196824 A1 * 10/2003 Gass ..................... B23B 45/008 173/131
2005/0109519 A1 * 5/2005 Kawai ................. B25B 23/1405 173/183
2005/0263304 A1 * 12/2005 Sainomoto .......... B25B 23/1405 173/176
2005/0279197 A1 * 12/2005 Wottreng .............. B25B 23/045 81/469
2007/0039301 A1 * 2/2007 Velke ................... A01D 34/824 56/10.8
2007/0119269 A1 * 5/2007 Anjanappa .......... B25B 23/1425 73/862.21
2007/0272423 A1 * 11/2007 Cutler ..................... B25B 23/14 173/1
2008/0017396 A1 * 1/2008 Kristen ................ B25D 16/006 173/162.2
2008/0251568 A1 * 10/2008 Zemlok ................ A61B 17/068 606/41
2009/0008111 A1 * 1/2009 Liebert ................ B25D 16/006 173/217
2009/0028652 A1 * 1/2009 Yamamoto .............. B25F 5/021 408/6
2009/0056965 A1 * 3/2009 Moessnang .......... B25D 16/006 173/18
2009/0200053 A1 * 8/2009 Scrimshaw ........... B23B 31/123 173/47
2010/0084151 A1 * 4/2010 Kuhnle .................... G05G 1/12 173/217
2010/0237124 A1 * 9/2010 Shima ....................... B25C 1/06 227/129
2011/0030980 A1 * 2/2011 Ho ........................ B23B 45/008 173/176
2012/0106133 A1 * 5/2012 Roehm ................... B25B 23/18 362/119
2013/0041284 A1 * 2/2013 Thompson ......... A61B 10/0275 600/563
2013/0126202 A1 * 5/2013 Oomori ................... B25B 21/00 173/217
2013/0274797 A1 * 10/2013 Nicholas .......... A61B 17/07207 227/175.1
2013/0331994 A1 * 12/2013 Ng ......................... G05B 15/02 700/275
2014/0006295 A1 * 1/2014 Zeiler .................. G06Q 30/018 705/317
2014/0165796 A1 * 6/2014 Gauthier ................ B25G 1/005 81/479
2014/0284070 A1 * 9/2014 Ng ............................ B25F 5/00 173/2
2014/0336684 A1 * 11/2014 Soeda ............ A61B 17/320783 606/159
2015/0014004 A1 * 1/2015 Schubert ................. B23B 49/00 173/1
2015/0137721 A1 * 5/2015 Yamamoto ................ H02P 6/08 318/400.15
2016/0052118 A1 * 2/2016 Rudolph ................. B25B 21/00 173/48
2017/0216986 A1 * 8/2017 Dey, IV ................. B23D 51/16
2018/0085906 A1 * 3/2018 Nitsch .................. B25D 16/006
2018/0143615 A1 * 5/2018 Aizawa ................ G05B 19/409
2019/0125608 A1 * 5/2019 Bush .................... A61H 1/0255
2019/0217460 A1 * 7/2019 Mahalingappa .......... B25F 5/02
2020/0078918 A1 * 3/2020 Yoshikane .............. B25F 5/026
2020/0197119 A1 * 6/2020 Zergiebel ............... A61B 34/74
2021/0387319 A1 * 12/2021 Chung ...................... B25F 5/00
2022/0190687 A1 * 6/2022 Fukuoka ................. B25B 23/18
2022/0226013 A1 * 7/2022 Hall ................... A61B 18/1445
2023/0118960 A1 * 4/2023 Arich ................... B25D 16/006 173/48
2023/0356382 A1 * 11/2023 Kamiya .................. B25F 5/026
2023/0404572 A1 * 12/2023 Rivard ................... G16H 30/40
2024/0000452 A1 * 1/2024 Du ................... A61B 17/07207
2024/0157538 A1 * 5/2024 Tan ......................... B25B 21/00
2024/0308034 A1 * 9/2024 Kamiya ................ B25B 21/026

* cited by examiner

FOOT REPAIR DEVICE

CROSS-REFERENCE TO RELATED APPLICATIONS

This application claims priority to Chinese Patent Application No. 202520833286.5, filed on Apr. 29, 2025, which is hereby incorporated by reference in its entirety.

TECHNICAL FIELD

The present disclosure relates to the field of foot repair tools technologies, and in particular, to a foot repair device.

BACKGROUND

With the improvement of living standards, people's demand for foot care is increasing day by day, and electric foot repairers have gradually become a commonly used tool for home care due to their efficient and convenient characteristics. Traditional electric foot repair devices commonly use a single speed regulation method: for example, segmented adjustment of the buttons requires the user to press a plurality of buttons continuously to reach the highest speed, or the mechanical knob is arranged at its end/designed as a rotatable adjustment knob. At the same time, the adjustment knob integrates functions such as power on/off, forward/reverse rotation, and speed regulation. When held, hands or fingers need to be adjusted. One handed operation stability is poor, operation is cumbersome, and the user has to remember too many instructions, which leads to the product being too long in size and unattractive in shape. In summary, the layout of control components in existing products is unreasonable: the speed control components are mostly located at the end or side of the housing, and the position of the fingers needs to be constantly adjusted to reach them when holding, and the stability of one-handed operation is poor. The separation of switches and speed control components results in redundant operation lines. Meanwhile, the operational status information (such as speed and battery level) often lacks intuitive display, or the display area is obstructed, which affects the user experience.

SUMMARY

The purpose of the present disclosure is to provide a foot repair device to meet the needs of users, in response to shortcomings of the existing technology mentioned above.

To achieve the above objectives, the present disclosure provides a foot repair device, including:

a housing, configured to form a handle, the handle includes a first handle end and a second handle end;

a foot repair device main body, which is accommodated in the housing and includes a driving motor, a battery, and a control component; the driving motor includes a driving shaft configured to extend out of the first handle end, and the battery is configured to supply power to the driving motor;

a functional head, which is connected to the driving shaft;

the control component includes a control circuit board, a switch button, and a speed control dial; where the switch button and the speed control dial are electrically connected to the control circuit board; the switch button is configured to control the start and stop of the driving motor; the speed control dial regulates a rotation speed of the functional head by adjusting an output rotation speed of the driving motor;

the switch button is movably embedded in the housing and is provided in a middle of the housing; and the speed control dial is capable of rotating relative to the housing and is provided on one side of the switch button and adjacent to the second handle end.

In some embodiments of the present disclosure, the control component further includes a display device configured to display an output rotation speed information of the driving motor and a battery level of the battery; the switch button and the speed control dial are respectively provided on two sides of the display device along an axis of the housing. The neat layout facilitates the integration and fixation of the control circuit board and connecting wires, optimizes the utilization of internal space, and forms a simple and smooth visual line, enhancing the overall appearance and aesthetics of the product.

In some embodiments of the present disclosure, the control component further includes a forward/reverse button, and the forward/reverse button is arranged to be adjacent to the switch button, and the forward/reverse button is configured to control a rotation direction of the driving shaft.

In some embodiments of the present disclosure, the speed control dial is configured to achieve a step change in the output rotation speed of the driving motor through discrete triggering.

In some embodiments of the present disclosure, the control component further includes an adjustment button configured to achieve a step change in the output rotation speed of the driving motor through discrete triggering, and the speed control dial configured to achieve linear adjustment of the output rotation speed of the driving motor through continuous rotation. By synergistically combining discrete step adjustment and continuous stepless adjustment, the technical synergy effect of precise speed fine-tuning (continuous mode) and fast mode switching (discrete mode) is achieved, thereby solving a technical contradiction of the inability to achieve both operational efficiency and adjustment accuracy in a single speed regulation method.

In some embodiments of the present disclosure, the housing includes:

an inner housing, which is provided with a main cavity, and the driving motor and the battery are provided in the same row inside the main cavity; the control circuit board is arranged parallel to the battery, and the inner housing includes a front housing and a rear housing that are docked and matched; the switch button, forward/reverse button, display device, and speed control dial are provided on an outer side of the front housing, and the control circuit board is provided on an inner side of the front housing, the outer housing, which is sleeved on an outer side of the inner housing and includes an avoidance area configured to expose the switch button, an adjustment button, the display device, and the speed control dial;

a limit curve housing, which is provided in the avoidance area, and the limit curve housing cooperates with the outer housing to form a continuous curved surface; the limit curve housing is sleeved on the display device and the speed control dial and is made of transparent or visible material for observation of the display device; the limit curve housing limits the speed control dial to prevent it from falling off.

In some embodiments of the present disclosure, the front housing is fastened to the rear housing, and the limit curved housing is fastened to the outer housing or the inner housing.

In some embodiments of the present disclosure, the front housing is inwardly recessed with a button slot, a display slot, and a dial slot; the switch button and the forward/reverse button are extendable up and down in the button slot, the display device is provided in the display slot, and the speed control dial is provided in the dial slot, and the dial slot is provided with two symmetrically arranged operation notches that are configured to expose a part of the speed control dial.

In some embodiments of the present disclosure, the housing is cylindrical, and the speed control dial is configured to rotate in a radial direction of the housing, where the speed control dial includes a dial surface and a first rotation shaft and a second rotation shaft extending from a center of the dial surface to two sides; the limit curve housing includes a first shaft sleeve configured to support the first rotation shaft, and the control circuit board includes a second shaft sleeve configured to support the second rotation shaft.

In some embodiments of the present disclosure, the speed control dial includes a conical surface extending downward around the dial surface, and the conical surface is provided with a plurality of recesses or convex ribs to enhance friction force when fingers in contact, and the conical surface is exposed out from the operation notches.

In some embodiments of the present disclosure, a forward projection of the speed control dial completely falls into a forward projection of the housing, and/or the speed control dial is conical in shape, and a maximum diameter of the speed control dial does not exceed a diameter of the housing so as to avoid protruding and have an interference with grip.

In some embodiments of the present disclosure, a surface of the functional head can be replaced with sandpaper of different grit sizes, and at least two different thicknesses of sandpaper will be provided for a user to use, aiming to solve the problem of traditional functional heads being unable to replace sandpaper, which poses a hygiene hazard and is prone to cross infection. The functional head has at least two shapes among cylindrical head, conical head, spherical head, hemispherical head, and disc-shaped head, and the functional heads of different shapes are interchangeably connected to the driving shaft. Cylindrical, conical, spherical, and hemispherical functional heads are suitable for small area polishing and nail polishing. The conical functional head is suitable for handling edges, corners, and difficult to reach areas of the foot, such as toe crevices and heel edges. The conical functional head can be penetrated these narrow areas for precise grinding and trimming. A disc-shaped functional head is typically used to handle larger areas such as the sole and surface of the foot. Smaller cylindrical functional heads can also be covered with rolled up sandpaper for polishing fingernails. It can be understood that those skilled in the art can easily conceive of forming the functional heads into different shapes to form foot repair accessories or nail repair accessories. Therefore, the specific shape of the functional heads should not constitute a limitation on the present disclosure.

In some embodiments of the present disclosure, at least one of the following conditions must be met:

an axial length H of the housing is 15 cm-20 cm;

a diameter of the housing ranges from 4 cm to 5 cm;

a width w of the switch button is 1 cm-2 cm;

a maximum diameter of the speed control dial is 3 cm-4 cm.

The beneficial effects of the present disclosure are as follows.

1. By providing the switch button in the middle of the housing and the speed dial being provided near the second handle end, the distribution is reasonable. The user can easily control the switch and adjust the speed without moving their fingers significantly during operation.

2. By providing the display device between the switch button and the speed control dial, coupled with a transparent/visible limit curved housing, the user can intuitively obtain key information such as driving motor speed and battery level without significantly shifting their line of sight when adjusting the speed or starting/stopping the device, thereby ensuring that parameters can be viewed directly in any grip position. The user can also conveniently and quickly set the appropriate rotation speed through the speed control dial and the speed information on the display screen. The positions of the speed control dial, switch button, and adjustment button are relatively fixed and easy to distinguish. The component layout is reasonable, and the functional zoning is clear. The user can accurately identify and operate corresponding components during operation, thereby reducing the possibility of user misoperation.

3. By arranging replaceable functional heads to improve applicability, different shaped functional heads can be used to handle different parts and problems of the foot, thereby achieving more precise and professional foot repair operations. Besides that, the surface of the functional head can be replaced with sandpaper of different grit sizes, which can achieve different degrees of grinding function while being clean and hygienic, thereby avoiding the hidden danger of cross infection. The user can also freely change the functional head according to preferences and actual needs, and obtain personalized foot repair experience.

Figure 1:
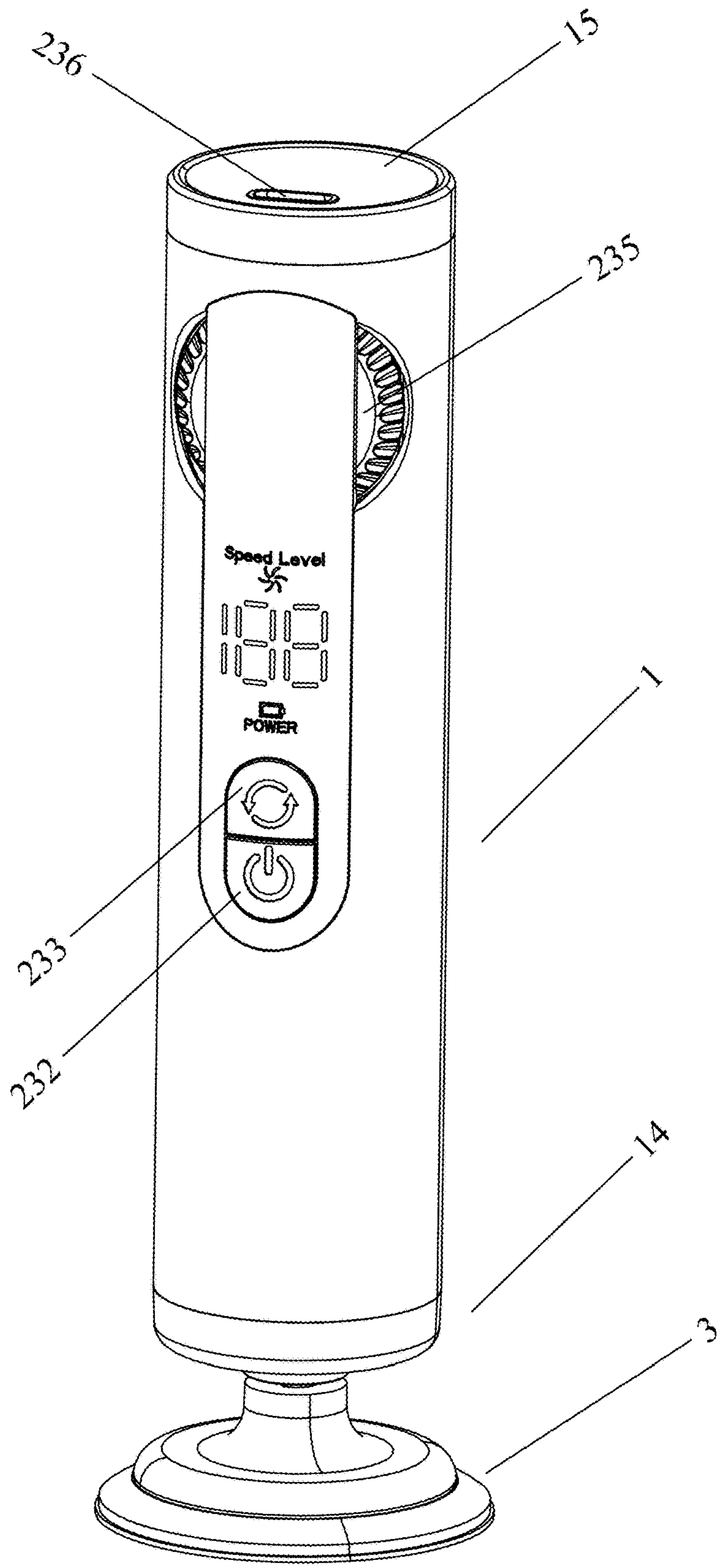
FIG. 1 is a schematic structural diagram of a foot repair device provided by the present disclosure.
Figure 2:
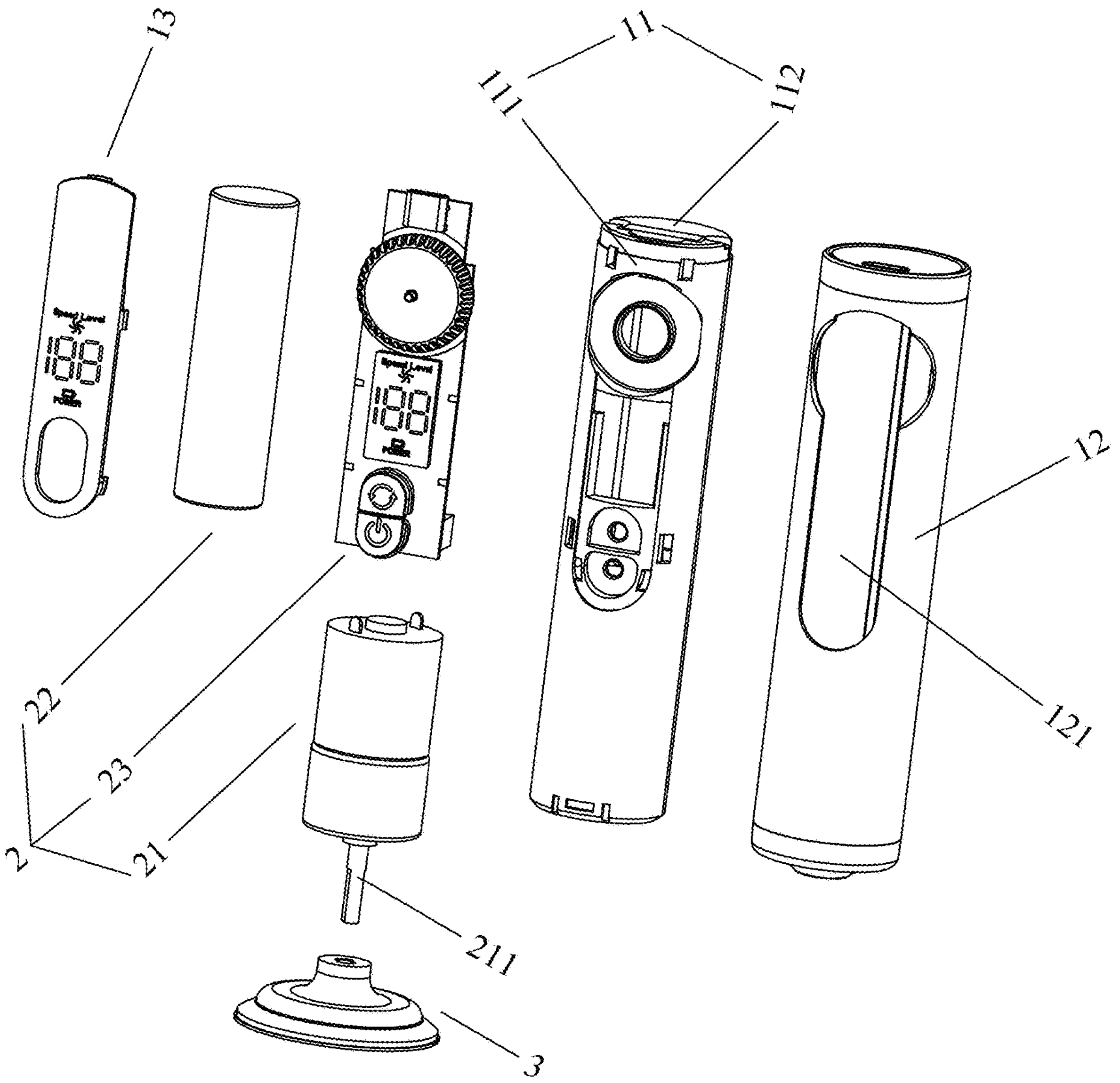
FIG. 2 is an exploded schematic diagram of the foot repair device provided by the present disclosure.
Figure 3:
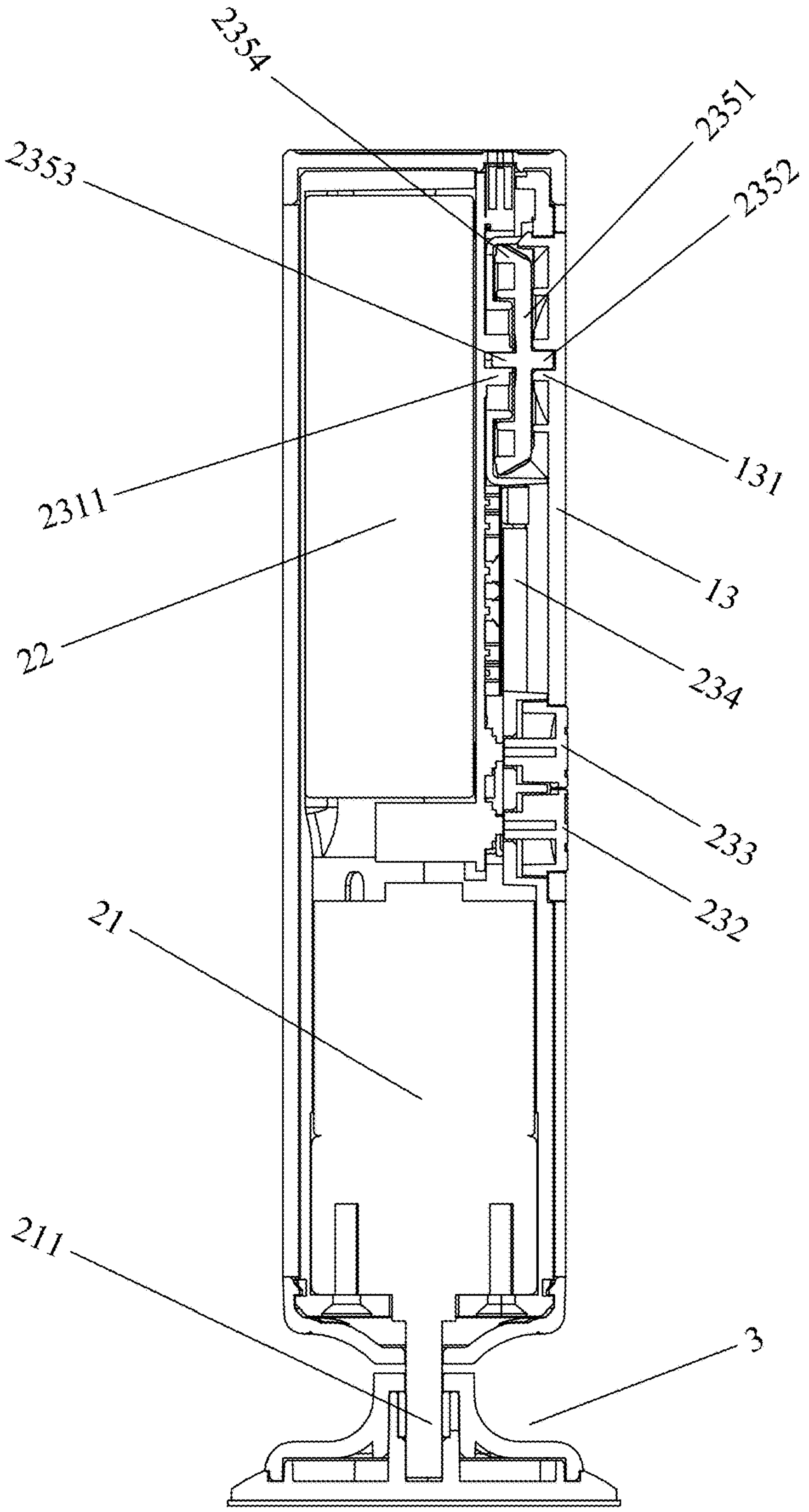
FIG. 3 is a schematic sectional view of the foot repair device provided by the present disclosure.
Figure 4:
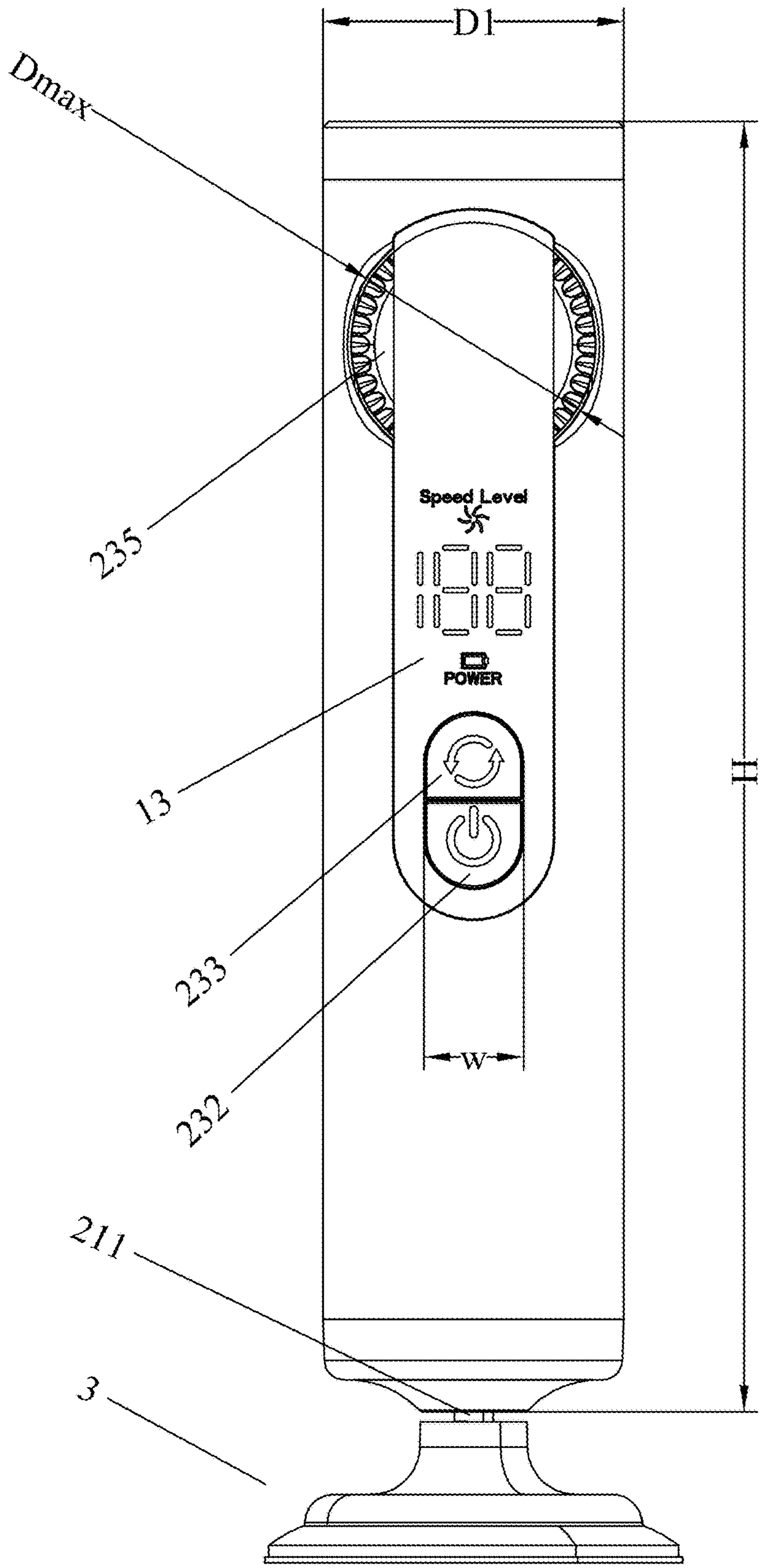
FIG. 4 is a front schematic diagram of the foot repair device provided by the present disclosure.
Figure 5:
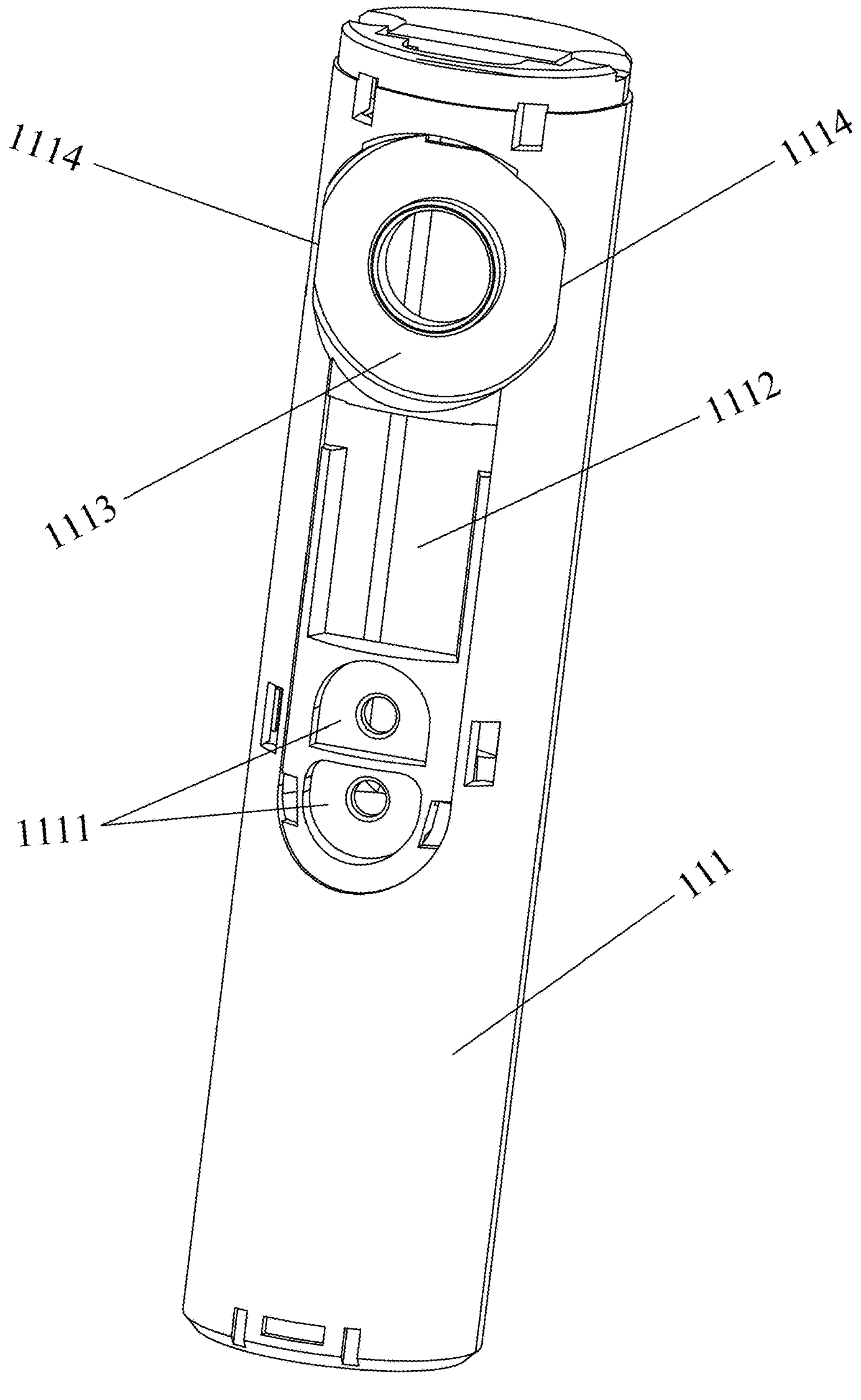
FIG. 5 is a schematic structural diagram of an inner housing provided by the present disclosure.
Figure 6:
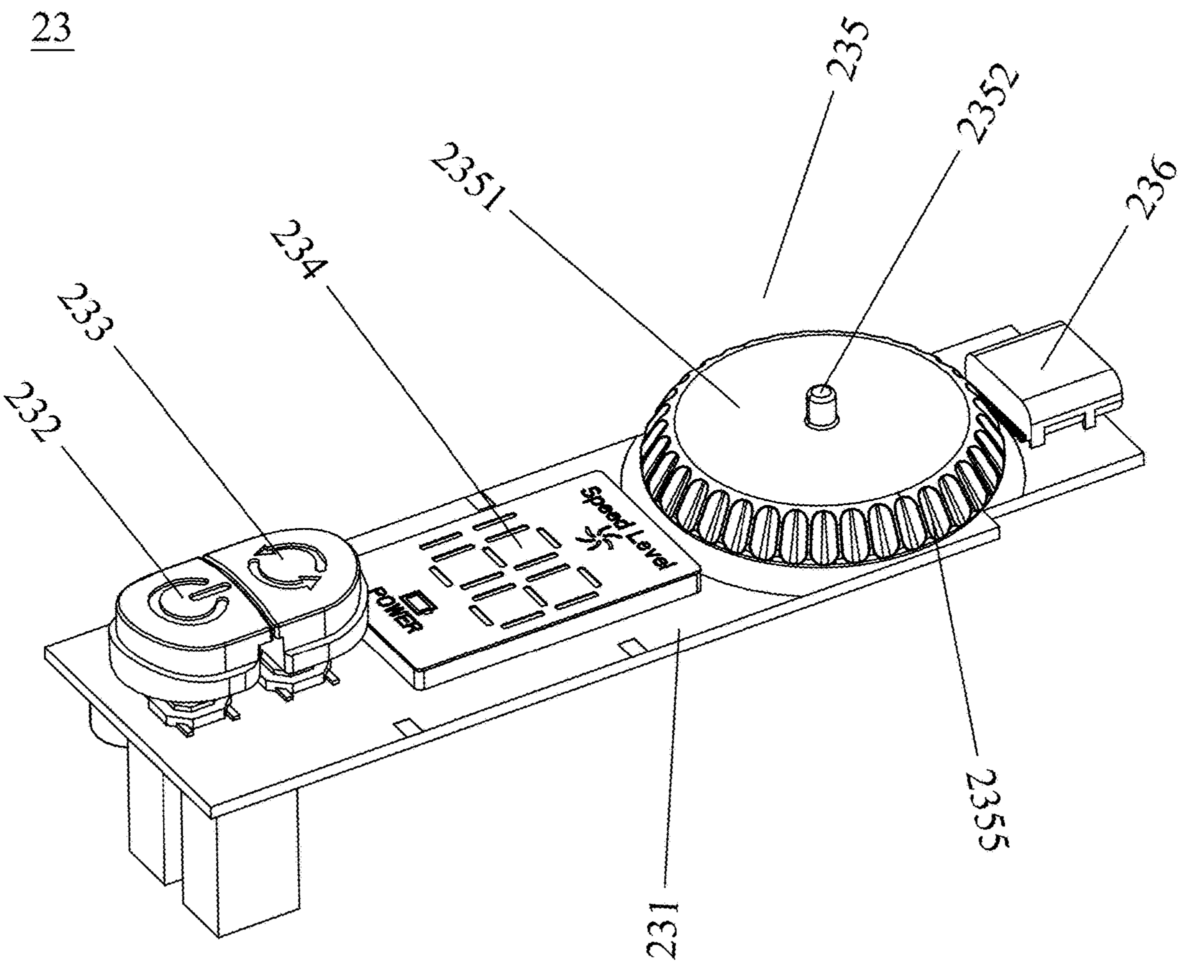
FIG. 6 is a schematic structural diagram of a control component provided by the present disclosure.

Numeral reference: 1—housing; 11—inner housing; 111—front housing; 1111—button slot; 1112—display slot; 1113—dial slot; 1114—operation notch; 112—rear housing; 113—main cavity; 12—outer housing; 121—avoidance area; 13—limit curve housing; 131—first shaft sleeve; 14—first handle end; 15—second handle end; 2—foot repair device main body; 21—driving motor; 211—driving shaft; 22—battery; 23—control component; 231—control circuit board; 2311—second shaft sleeve; 232—switch button; 233—forward/reverse button; 234—display device; 235—speed control dial; 2351—dial surface; 2352—first rotation shaft; 2353—second rotation shaft; 2354—conical surface; 2355—recess; 236—charging interface; 3—functional head.

DESCRIPTION OF EMBODIMENTS

In order to clarify the purpose, technical solution, and advantages of the present disclosure, a detailed description of the present disclosure will be provided below in combination with the accompanying drawings and specific embodiments.

Here, it should be noted that in order to avoid blurring the present disclosure due to unnecessary details, only the structures and/or processing steps closely related to the solution of the present disclosure are shown in the accompanying drawings, and other details that are not closely related to the present disclosure are omitted.

Besides that, it should be noted that terms “including”, “comprising”, or any other variation thereof are intended to encompass non-exclusive inclusion, such that a process, method, item, or device that includes a series of elements not only includes those elements, but also includes other elements that are not explicitly listed or are inherent to such a process, method, item, or device.

As shown in FIGS. 1-6, a foot repair device includes a housing 1, a foot repair device main body 2, and a functional head 3. The housing 1 is configured to form a handle that can be held, and the handle includes a first handle end 14 and a second handle end 15. The foot repair device main body 2 is accommodated in the housing 1 and includes a driving motor 21, a battery 22, and a control component 23. The driving motor 21 includes a driving shaft 211 configured to extend out from the first handle end 14, and the functional head 3 is detachably connected to the driving shaft 211. The first handle end 14 has an approximate funnel shape, which can serve as a decorative element for the driving shaft 211, rendering the product more aesthetically pleasing. The battery 22 is configured to supply power to the driving motor 21. The control component 23 includes a control circuit board 231, a switch button 232, a forward/reverse button 233, a display device 234, and a speed control dial 235 that are electrically connected to the control circuit board 231. From the second handle end 15 towards the first handle end 14, the speed control dial 235, display device 234, forward/reverse button 233, and forward/reverse button 233 are arranged in sequence. The switch button 232 is provided in a middle of the housing 1. The switch button 232 is movably embedded in the housing 1 and is configured to control start and stop of the driving motor 21. The forward/reverse button 233 is configured to control a rotation direction of the driving shaft 211. The speed control dial 235 can be rotated relative to the housing 1. The speed control dial 235 achieves a step change in an output rotation speed of the driving motor 21 through a discrete triggering mode, thereby regulating a rotation speed of the functional head 3. The display device 234 is configured to display an output rotation speed information of the driving motor 21 and a battery level of the battery 22. The second handle end 15 is provided with a charging interface 236 configured to charge the battery 22, and the charging interface 236 is electrically connected to the control circuit board 231.

In an implementation mode, the output rotation speed of the driving motor 21 is set to 10 gears. When the speed of the control dial 235 is slowly turned, the number representing the speed gear displayed on the display device 234 is gradually increased/decreased, corresponding to the gradual increase/decrease of the output rotation speed step by step. If the speed control dial 235 is quickly turned, the number representing the speed gear displayed on the display device 234 will be changed rapidly (such as jumping from 1st gear to 8th gear at once).

In an implementation mode, the housing 1 is cylindrical and includes an inner housing 11, an outer housing 12, and a limit curve housing 13. The inner housing 11 includes a front housing 111 and a rear housing 112 that are connected and fastened together, as well as a main cavity 113 defined by the two. The driving motor 21 and the battery 22 are arranged in the same row in the main cavity 113, and the control circuit board 231 is arranged parallel to the battery 22. The front housing 111 is inwardly recessed provided with a button slot 1111, a display slot 1112, and a dial slot 1113. The switch button 232 and the forward/reverse button 233 are extendable up and down in the button slot 1111. The display device 234 is provided in the display slot 1112, and the speed control dial 235 is provided in the dial slot 1113. The dial slot 1113 is provided with two symmetrically arranged operation notches 1114 that are configured to expose a part of the speed control dial 235. The control circuit board 231 is provided on an inner side of the front housing 111.

In an implementation mode, the speed control dial 235 is in a shape of a round platform and includes a dial surface 2351, a first rotation shaft 2352 and a second rotation shaft 2353 extending from a center of the dial surface 2351 to two sides, and a conical surface 2354 extending downward around the dial surface 2351. The limit curve housing 13 includes a first shaft sleeve 131 configured to support the first rotation shaft 2352, and the control circuit board 231 includes a second shaft sleeve 2311 configured to support the second rotation shaft 2353. The speed control dial 235 is configured to rotate in a radial direction of the housing 1. The speed control dial 235 includes a conical surface 2354 with a plurality of recesses 2355 to enhance a friction force when fingers being in contact. The conical surface 2354 is exposed out from the operation notches 1114.

In an implementation mode, the outer housing 12 is sleeved on an outer side of the inner housing 11 and includes an avoidance area 121 configured to expose the switch button, forward/reverse button 233, display device 234, and speed control dial 235. The limit curve housing 13 is fastened to the inner housing 11 and provided in the avoidance area 121. The limit curve housing 13 cooperates with the outer housing 12 to form a continuous curved surface. The limit curve housing 13 is sleeved on the display device 234 and is made of transparent material for easy observation of the display device 234. Besides that, the outer housing 12 is detachably connected to a top of the inner housing 11 and forms a limit along its axial direction. The limit curve housing 13 is installed last.

In an implementation mode, a front projection of the speed control dial 235 completely falls into a front projection of the housing 1. A maximum diameter of the speed control dial 235 should not exceed a diameter of the housing 1 to avoid being protruded and having an interference with grip. An axial length H of the handle is 18 cm, a diameter of the handle is 4.8 cm, a width w of the switch button is 1.5 cm, and a maximum diameter of the speed control dial 235 is 3.6 cm.

In an implementation mode, the speed control dial 235 can realize a linear adjustment of the output rotation speed of the driving motor 21 through continuous rotation, and the adjustment button can realize the step change of the rotation speed through discrete triggering, which is convenient for fast switching of the speed mode. The combination of the two enables the foot repair device to quickly switch to the appropriate speed range and make precise adjustments to adapt to different foot care scenarios.

Figure 7:
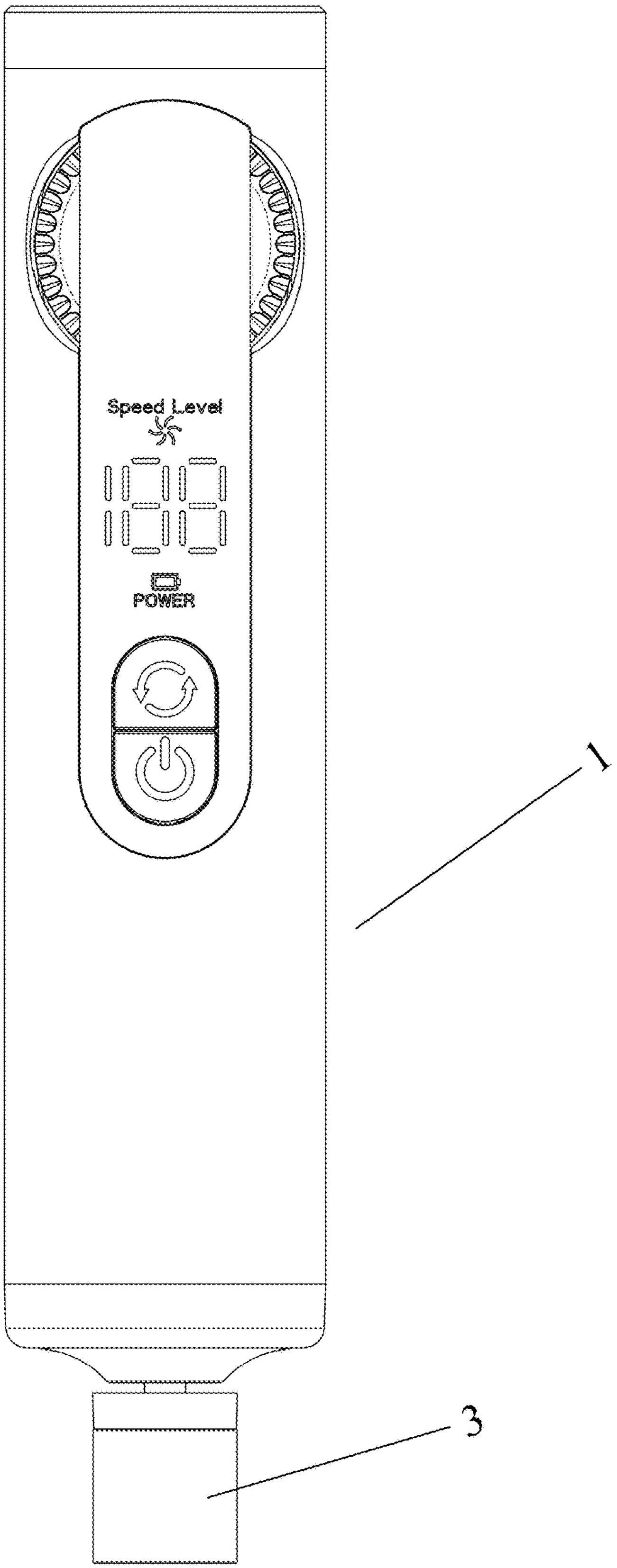
FIG. 7 is a schematic diagram of the foot repair device with a cylindrical functional head provided by the present disclosure.

In an implementation mode, a surface of the functional head 3 can be replaced with sandpaper of different mesh sizes, which can achieve different degrees of grinding function while being clean and hygienic, thereby avoiding a hidden danger of cross infection. The functional head 3 includes a cylindrical functional head (FIG. 7) and a disc-shaped functional head (FIG. 1). The function head 3 and the driving shaft 211 are configured to be inserted and extracted along their axial direction.

In summary, the speed control dial 235 is provided on one side of the switch button 232 and adjacent to the second handle end 15. A collaborative layout of the switch button 232 and the forward/reverse button 233 achieves a coordinated coordination of discrete step adjustment and continuous stepless adjustment. When the user holds the foot repair device with one hand for use, the product is gripped like holding a pen. If grinding the feet of others, it is like holding a flashlight. The thumb and index finger can naturally touch the speed dial and switch button respectively, thereby forming an efficient operation mode of "thumb speed control-index finger control start-and-stop", thereby reducing grip posture adjustment and reducing operational fatigue.

The above embodiments are only used to illustrate the technical solution of the present disclosure and not to limit it. Although the present disclosure has been described in detail with reference to preferred embodiments, those skilled in the art should understand that the technical solution of the present disclosure can be modified or equivalently replaced without departing from the spirit and scope of the technical solution of the present disclosure.

What is claimed is:

1. A foot repair device, comprising:

a housing, configured to form a handle, the handle comprises a first handle end and a second handle end;

a foot repair device main body, which is accommodated in the housing and comprises a driving motor, a battery, and a control component; the driving motor comprises a driving shaft configured to extend out of the first handle end, and the battery is configured to supply power to the driving motor;

a functional head, which is connected to the driving shaft;

the control component comprises a control circuit board, a switch button, and a speed control dial; wherein the switch button and the speed control dial are electrically connected to the control circuit board; the switch button is configured to control the start and stop of the driving motor; the speed control dial regulates a rotation speed of the functional head by adjusting an output rotation speed of the driving motor;

the switch button is movably embedded in the housing and is provided in a middle of the housing; and the speed control dial is capable of rotating relative to the housing and is provided on one side of the switch button and adjacent to the second handle end;

wherein the housing comprises a limit curve housing;

wherein the housing is cylindrical, and the speed control dial is configured to rotate in a radial direction of the housing, wherein the speed control dial comprises a dial surface, a first rotation shaft and a second rotation shaft extending from a center of the dial surface to two sides, the limit curve housing comprises a first shaft sleeve configured to support the first rotation shaft, and the control circuit board comprises a second shaft sleeve configured to support the second rotation shaft.

2. The foot repair device according to claim 1, wherein the control component further comprises a display device configured to display an output rotation speed information of the driving motor and a battery level of the battery;

the switch button and the speed control dial are respectively provided on two sides of the display device along an axis of the housing.

3. The foot repair device according to claim 2, wherein the control component further comprises a forward/reverse button, and the forward/reverse button is arranged to be adjacent to the switch button, and the forward/reverse button is configured to control a rotation direction of the driving shaft.

4. The foot repair device according to claim 3, wherein the housing comprises:

an inner housing, which is provided with a main cavity, and the driving motor and the battery are provided in the same row inside the main cavity; the control circuit board is arranged parallel to the battery, and the inner housing comprises a front housing and a rear housing that are docked and matched;

the switch button, forward/reverse button, display device, and speed control dial are provided on an outer side of the front housing, and the control circuit board is provided on an inner side of the front housing, and an outer housing, which is sleeved on an outer side of the inner housing and comprises an avoidance area configured to expose the switch button, an adjustment button, the display device, and the speed control dial;

wherein the limit curve housing is provided in the avoidance area, and the limit curve housing cooperates with the outer housing to form a continuous curved surface; the limit curve housing is sleeved on the display device and the speed control dial and is made of transparent or visible material for observation of the display device; the limit curve housing limits the speed control dial to prevent it from falling off.

5. The foot repair device according to claim 4, wherein the front housing is inwardly recessed with a button slot, a display slot, and a dial slot, the switch button and the forward/reverse button are extendable up and down in the button slot, the display device is provided in the display slot, and the speed control dial is provided in the dial slot, and the dial slot is provided with two symmetrically arranged operation notches that are configured to expose a part of the speed control dial.

6. The foot repair device according to claim 1, wherein the speed control dial comprises a conical surface extending downward around the dial surface, and the conical surface is provided with a plurality of recesses or convex ribs, and the conical surface is exposed out from the operation notches.

7. The foot repair device according to claim 6, wherein a forward projection of the speed control dial completely falls into a forward projection of the housing, and/or the speed control dial is conical in shape, and a maximum diameter of the speed control dial does not exceed a diameter of the housing.

8. The foot repair device according to claim 1, wherein the functional head has at least two shapes among cylindrical head, conical head, spherical head, hemispherical head, and disc-shaped head, and the functional heads of different shapes are interchangeably connected to the driving shaft.

* * * * *